United States Patent [19]
Berry, Jr.

[11] Patent Number: 5,918,740
[45] Date of Patent: Jul. 6, 1999

[54] INSTRUMENT CASSETTE

[75] Inventor: Bernie B. Berry, Jr., Indianapolis, Ind.

[73] Assignee: Carr Metal Products, Inc., Indianapolis, Ind.

[21] Appl. No.: 08/851,594

[22] Filed: May 5, 1997

[51] Int. Cl.$^6$ .................................................. B65D 81/18
[52] U.S. Cl. ......................... 206/369; 206/370; 220/326; 422/300
[58] Field of Search .................................. 206/210, 363, 206/370, 439, 508, 369; 220/326; 422/297, 300

[56] References Cited

U.S. PATENT DOCUMENTS

| | | |
|---|---|---|
| 857,240 | 6/1907 | Henning . |
| 1,918,664 | 7/1933 | Rasmusson .............................. 220/326 |
| 3,285,409 | 11/1966 | Loran . |
| 4,541,992 | 9/1985 | Jerge et al. . |
| 4,643,303 | 2/1987 | Arp et al. . |
| 4,774,063 | 9/1988 | Runnells . |
| 4,798,292 | 1/1989 | Hauze . |
| 4,801,039 | 1/1989 | McCall et al. .......................... 220/326 |
| 4,818,502 | 4/1989 | Taschner ................................. 220/326 |
| 4,826,348 | 5/1989 | Brightman . |
| 4,854,475 | 8/1989 | Riihimaki et al. . |
| 4,930,660 | 6/1990 | Porteous . |
| 4,959,199 | 9/1990 | Brewer . |
| 5,002,319 | 3/1991 | Chandler . |
| 5,031,768 | 7/1991 | Fischer . |
| 5,084,251 | 1/1992 | Thomas . |
| 5,174,453 | 12/1992 | Stoeffler ................................. 206/370 |
| 5,215,726 | 6/1993 | Kudla et al. . |
| 5,267,668 | 12/1993 | Jones ...................................... 220/326 |
| 5,279,800 | 1/1994 | Berry, Jr. . |
| 5,294,413 | 3/1994 | Riihimaki et al. ...................... 206/370 |
| 5,346,677 | 9/1994 | Risk . |
| 5,384,103 | 1/1995 | Miller .................................... 206/508 |
| 5,505,916 | 4/1996 | Berry, Jr. . |
| 5,533,642 | 7/1996 | Lafond et al. .......................... 220/326 |

FOREIGN PATENT DOCUMENTS 805909  6/1951  Germany .

OTHER PUBLICATIONS

"Specifications for the Combined Endo–Rubber Dam and Restorative/Rubber Dam Cassettes", published by the University of Maryland at Baltimore, Office of Procurement and Supply, 737 W. Lombard Street, Baltimore, Maryland 21201–1041, under Solicitation No. IFB80865JL1, Mar. 25, 1996, 9 pages.

*Primary Examiner*—Jim Foster
*Attorney, Agent, or Firm*—Woodard, Emhardt, Naughton Moriarty & McNett

[57] ABSTRACT

An autoclavable instrument cassette for receiving and storing medical and dental instruments and equipment includes a separable tray and lid combination. The tray and lid are each configured with a plurality of sterilant apertures in order to facilitate the autoclaving of whatever instruments and equipment may be stored inside. The tray is configured with a plurality of separate compartments which are defined by various dividers. A lift-out rack is included and arranged for retaining a plurality of instruments. The lid is arranged with a finger mat in order to cooperate with the lift-out rack for securing the instruments in position. The lid also includes a plurality of retainers which are moveable and designed to accommodate a variety of instruments which can be retained in the lid. The tray and lid are secured together by a latch pin assembly which is secured to the tray and includes a latch pin which extends through an opening in the lid. A pair of cooperating retaining pins mounted to the tray and extending through openings in the lid provide for the secure attachment of the lid to the tray, in cooperation with the latch pin assembly, and for the removal of the lid from the tray by pushing inwardly on the latch pin.

7 Claims, 8 Drawing Sheets

INSTRUMENT CASSETTE

BACKGROUND OF THE INVENTION

The present invention relates in general to a medical/dental instrument cassette for use in storing and retaining a variety of instruments and equipment used in medical and/or dental procedures. The instrument cassette according to the present invention is suitable for use throughout the washer, decontamination, and sterilization cycle. More specifically, the present invention relates to a medical/dental instrument cassette which is designed with the unique combination of features including a latch design which will not puncture the sterile paper wrapping.

Instrument cassettes which are used for the sterilization of medical and dental instruments and equipment have been designed in a variety of shapes and styles with a variety of features. The following listed patents provide a representative sampling of these earlier designs.

U.S. PATENTS

| U.S. PAT. NO. | PATENTEE | ISSUE DATE |
| --- | --- | --- |
| 5,279,800 | Berry, Jr. | Jan. 18, 1994 |
| 5,505,916 | Berry, Jr. | Apr. 4, 1996 |
| 4,798,292 | Hauze | Jan. 17, 1989 |
| 4,959,199 | Brewer | Sep. 25, 1990 |
| 5,084,251 | Thomas | Jan. 28, 1992 |
| 4,854,475 | Riihimaki et al. | Aug. 8, 1989 |
| 857,240 | Henning | Jun. 18, 1907 |
| 4,774,063 | Runnells | Sep. 27, 1988 |
| 5,346,677 | Risk | Sep. 13, 1994 |
| 5,215,726 | Kudla et al. | Jun. 1, 1993 |
| 4,930,660 | Porteous | Jun. 5, 1990 |
| 4,541,992 | Jerge et al. | Sep. 17, 1985 |
| 3,285,409 | Loran | Nov. 15, 1966 |
| 5,031,768 | Fischer | Jul. 16, 1991 |
| 4,643,303 | Arp et al. | Feb. 17, 1987 |
| 4,826,348 | Brightman | May 2, 1989 |

FOREIGN PATENTS

| PAT. NO. | COUNTRY | DATE |
| --- | --- | --- |
| 805,909 | Germany | Jun. 4, 1951 |

When an instrument cassette of the type represented by the listed patents is loaded with instruments and equipment for sterilization, it is important to provide appropriate retainers and storage mechanisms for the items. At the conclusion of the sterilization cycle, the loaded cassette is wrapped with paper as a sterilization wrapping in order to maintain the sterilized condition of the instruments and equipment which have been loaded into the cassette. One of the post-sterilization concerns is maintaining the integrity of the sterilization wrapping. If the wrapping is torn or punctured, atmospheric "dirty" air is able to enter and can contaminate the sterile instruments and equipment. It is therefore important that the cassette be designed without sharp corners and edges and without any protruding portions which could puncture the sterilization wrapping. Part of the concern over punctures is associated with the handling of the cassette. If there is a protruding portion or some sharp edge or corner, such as what might be present with a latch or hinge mechanism, a puncture can occur as the cassette is being wrapped. Even if a puncture does not occur during the wrapping process, a puncture can occur later when the wrapped cassette is handled to place the cassette into storage or remove it from storage. It is conceivable that the individual handling the cassette could grasp it in such a way so as to push the sterilization wrapping inwardly. If this is done in the proximity of a protruding portion, a sharp corner, or a sharp edge, a puncture of the wrapping can occur. As will be appreciated from a review of the listed patents, protruding portions from latches and hinge arrangements are quite common.

It is also important for the lid and tray combination to remain locked together during the washer, decontamination, and sterilization cycle. However, when the loaded cassette is selected for a particular procedure, it is important to be able to separate the lid from the tray with an appropriate break-away design.

Another concern with the design of medical/dental instrument cassettes is their ability to receive and retain a variety of instruments and equipment. The greater the design versatility and flexibility, the greater the number of procedures which can be accommodated by the cassette design. By arranging the cassette with more "generic" racks, compartments, and holders, the same style of cassette can be used for any one (or more) of several medical and/or dental procedures. For example, the cassette of the present invention can be loaded in one configuration with all of the required instruments and equipment for an endodontic procedure. The same cassette design can also be loaded with a slightly different group of instruments and equipment for a different procedure such as a restorative procedure. Additionally, the cassette of the present invention is equally suitable for a rubber dam procedure.

With the present invention, not only is this design versatility provided, but the present invention incorporates a novel combination of features including a latch design which will not puncture the sterilization wrapping. Notwithstanding the wide variety of earlier cassette designs, the present invention is novel and unobvious.

SUMMARY OF THE INVENTION

An autoclavable instrument cassette for receiving and storing medical and dental instruments and equipment according to one embodiment of the present invention comprises a tray configured with a plurality of separate compartments and including a plurality of sterilant apertures, a lid constructed and arranged to attach to the tray and to be separable from the tray, the lid including a plurality of sterilant apertures and a latch pin opening, and a latch pin assembly secured to the tray, the latch pin assembly including a latch pin which is constructed and arranged to extend into the latch pin opening when the lid is closed onto the tray, the latch pin having a free end which is the only portion of the latch pin assembly which extends into the lid.

One object of the present invention is to provide an improved autoclavable instrument cassette.

Related objects and advantages of the present invention will be apparent from the following description.

DESCRIPTION OF THE PREFERRED EMBODIMENT

Figure 1:
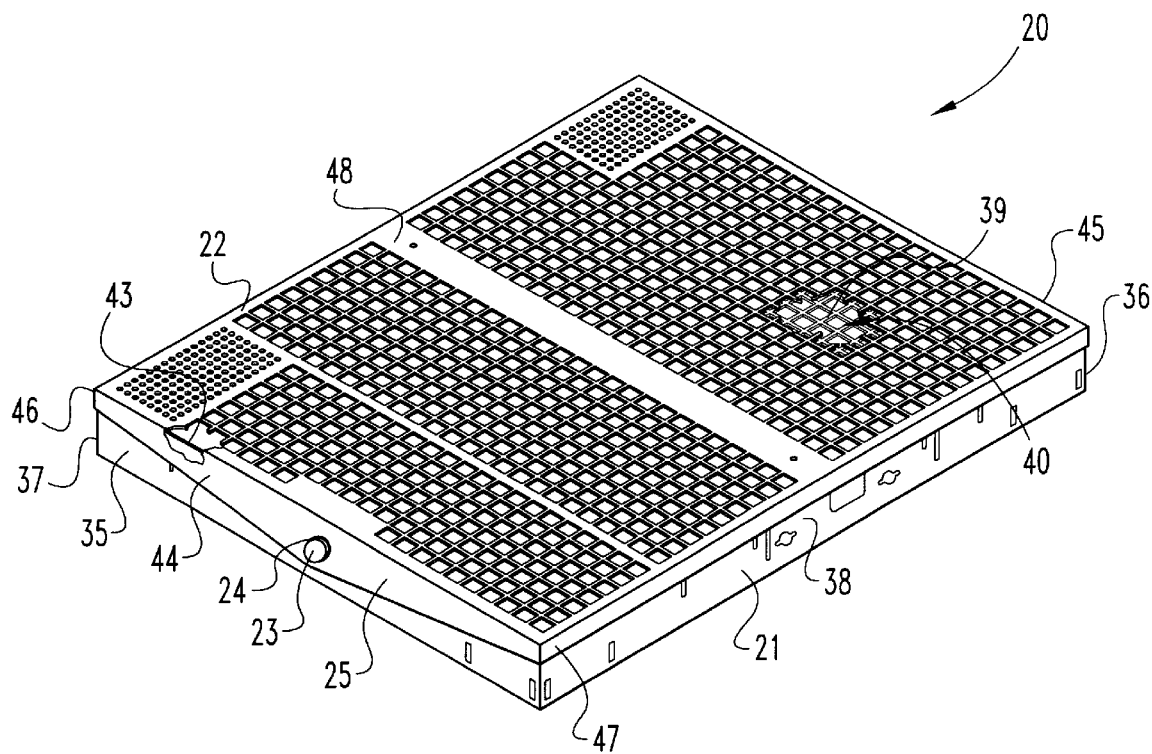
FIG. 1 is a right side perspective view of an instrument cassette according to a typical embodiment of the present invention.
Figure 2:
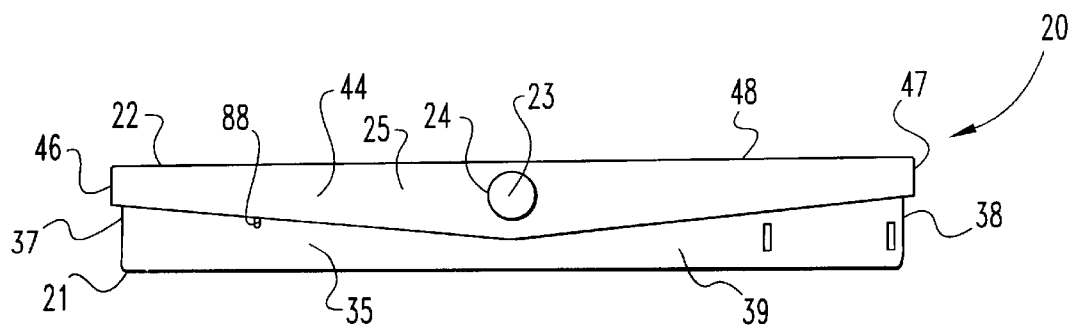
FIG. 2 is a right side elevational view of the FIG. 1 instrument cassette.
Figure 3:
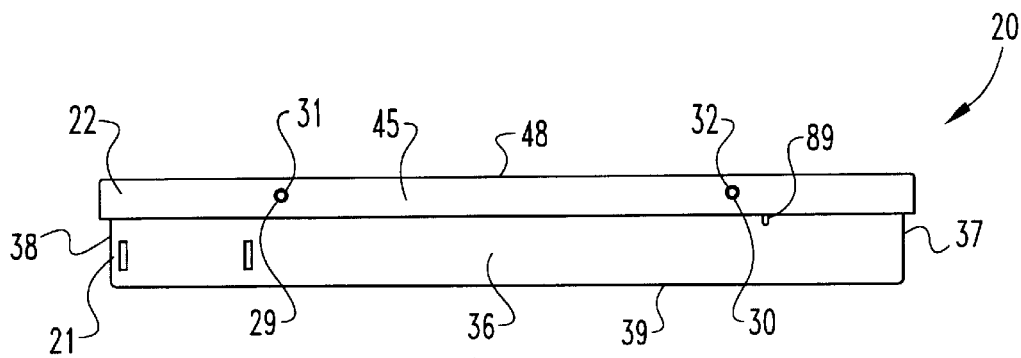
FIG. 3 is a left side elevational view of the FIG. 1 instrument cassette.
Figure 4:
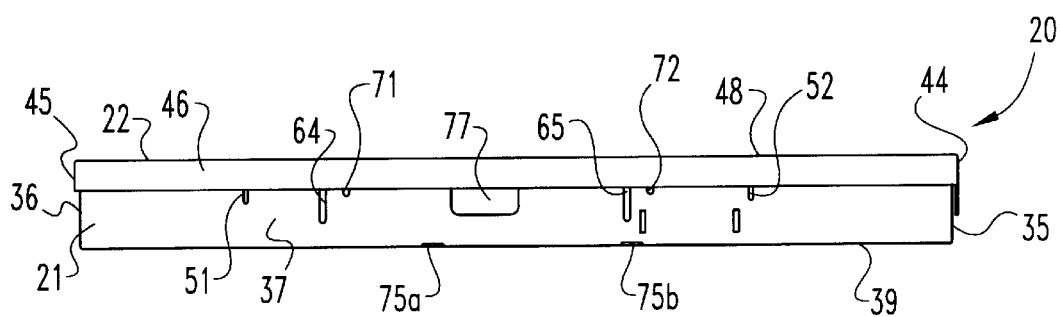
FIG. 4 is a front elevational view of the FIG. 1 instrument cassette.
Figure 5:
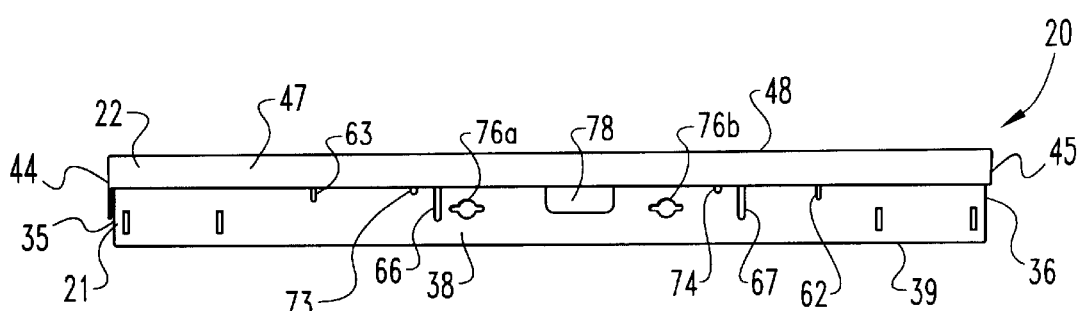
FIG. 5 is a rear elevational view of the FIG. 1 instrument cassette.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to FIGS. 1–5, a medical/dental instrument cassette 20 which is designed according to the present invention is illustrated. Cassette 20 includes a tray 21 and a cooperating lid 22. Latch pin 23 is attached to a latch bar which is attached to tray 21 and protrudes through opening 24 in the sidewall lip portion 25 of lid 22. The opposite side of the cassette (see FIG. 3) includes a pair of securing or retaining pins 29 and 30 which are attached to tray 21 and extend through lid openings 31 and 32, respectively. The use of securing or retaining pins 29 and 30 in cooperation with the two openings 31 and 32 and the design of latch pin 23 provides both a locked configuration and a break away design for completely separating the lid from the tray.

Figure 6:
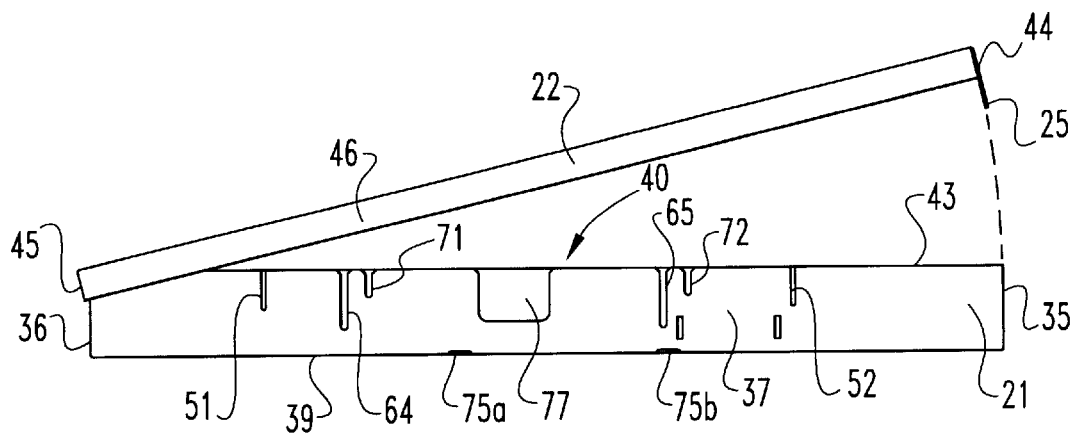
FIG. 6 is a front elevational view of the FIG. 1 instrument cassette with the lid in an opened condition.

With each of the three pins extending minimally through their corresponding openings, the tray and lid are locked together and are unable to be separated by simply trying to pull apart the two components. In order to separate the lid 22 from the tray 21, the first step is to push pin 23 inwardly until the outer end of the pin 23 clears opening 24. At this point the lid is able to be lifted up away from tray 21 (see FIG. 6). There is enough clearance between pins 29 and 30 and their corresponding openings 31 and 32 in order to permit the pivoting action of the lid 22 up and away from the right sidewall 35 of tray 21. With the lid 22 partially lifted, the lid 22 can be pushed in the direction of the left sidewall 36 of tray 21 which frees openings 31 and 32 off of pins 29 and 30. This then separates lid 22 from the tray 21.

Tray 21 is substantially rectangular in shape with four substantially rectangular sidewalls 35, 36, 37, and 38 and a substantially rectangular base panel 39. In combination, the base panel and the four sidewalls which extend upwardly from and around the base panel define an interior space 40 which is configured with various compartments and holders for receiving and retaining a variety of medical/dental instruments and equipment. Each sidewall is of substantially the same height so as to define a substantially planar top edge 43.

The substantially rectangular lid 22 includes four substantially planar sidewalls 44–47, three of which (44, 46, and 47) are each substantially rectangular and one of which, right sidewall 44, includes depending lip portion 25. Each sidewall is formed as to extend downwardly from and around planar top panel 48. In the assembled condition of FIG. 1, the four planar sidewalls 44–47 of the lid fit over the exterior surface of the four sidewalls 35–38 of the tray. By making the rectangular size of lid 22 slightly larger than the size of tray 21, in order to achieve the assembled configuration, the top panel 48 seats on the top edge 43 when the lid is closed and latched.

Figure 10:
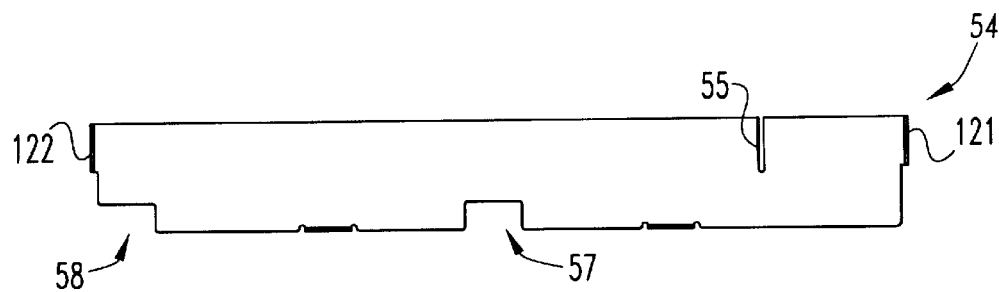
FIG. 10 is a front elevational view of a divider comprising a portion of the FIG. 1 instrument cassette.
Figure 10A:
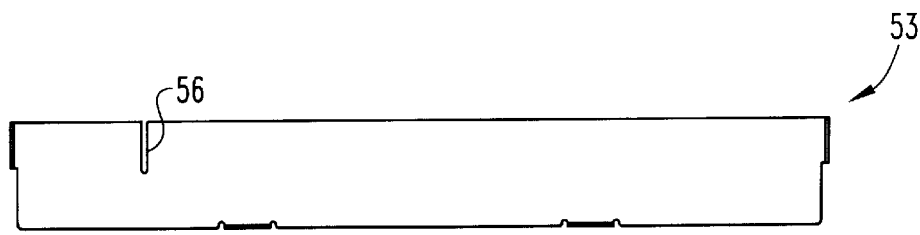
FIG. 10a is a front elevational view of a second divider style comprising a portion of the FIG. 1 instrument cassette.
Figure 11:
FIG. 11 is a top plan view of the FIG. 10 divider.
Figure 12:
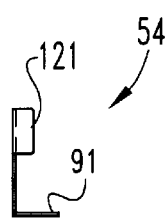
FIG. 12 is a side elevational view of the FIG. 10 divider.

The front sidewall 37 of tray 21 and the rear sidewall 38 of tray 21 are each configured with various slots and relief notches for the receipt and assembly of other components which are installed on the interior of tray 21. The front sidewall 37 includes two vertical slots 51 and 52, each of which is designed to receive a tab portion of a corresponding interior divider 53 and 54, respectively (see FIGS. 7, 10–12). Dividers 53 and 54 are virtually identical to each other except for the location of slots 55 and 56 and except for relief areas 57 and 58 which are part of divider 54 but are not part of divider 53. Each divider is substantially planar with exception of the two end tabs which are used for assembly and two base mounting tabs. Divider 53 is illustrated in FIG. 10A while divider 54 is illustrated in FIG. 10. FIGS. 11 and 12, while specifically identified as divider 54 views, correspond as well to divider 53. The rear sidewall 38 also includes two vertical slots 62 and 63 and each slot receives a corresponding tab portion of each divider 53 and 54, respectively. As illustrated, slots 51 and 62 are aligned with each other as are slots 52 and 63 such that dividers 53 and 54 are positioned so as to be substantially parallel to the right and left sidewalls 35 and 36.

The front and rear sidewalls 37 and 38 each include a four-slot pattern including a spaced-apart pair of deeper slots and a spaced-apart pair of shallow slots. The deeper slots 64 and 65 in front sidewall 37 have a location and spacing which corresponds to deeper slots 66 and 67 in rear sidewall 38. These four slots generally correspond to the spacing of four corner tabs on lift-out frame 68 (see FIG. 16). Frame 68 is substantially rectangular and configured with sixteen receiving channels in each side rail for receiving and retaining various medical/dental instruments.

The shallow slots 71 and 72 in front sidewall 37 have a location and spacing which corresponds to shallow slots 73 and 74 in rear sidewall 38. These four slots generally correspond to the spacing of four corner tabs in frame 68. Accordingly, the spacing between each adjacent pair of one deeper slot and one shallow slot is the same at the two locations in front sidewall 37 as well as at the two locations in rear sidewall 38. By providing two different four-slot patterns, frame 68 can be positioned lower to base panel 39 by using slots 64–67 or frame 68 can be mounted in a higher or raised location by using slots 71–74. By designing the deeper and the shallow slots with a sufficient depth difference, it is possible to stack two frames 68, one on top of the other, with only a slight side-to-side stagger. The stagger distance is equal to the distance between each deeper slot and its corresponding shallow slot at each corner of the frame 68. If two lift-out frames are present, the upper lift-out frame is positioned vertically to clear instruments in the lower frame, while still retaining the instruments in the individual positioning channels.

Relief areas 77 and 78 provide finger clearance areas in order to be able to manually and easily lift frame 68 out of its retained position in the opposite sidewalls. These relief areas provide adequate finger clearance, regardless of which sets of slots are used to receive frame 68 or even if a pair of stacked frames are present.

Figure 20:
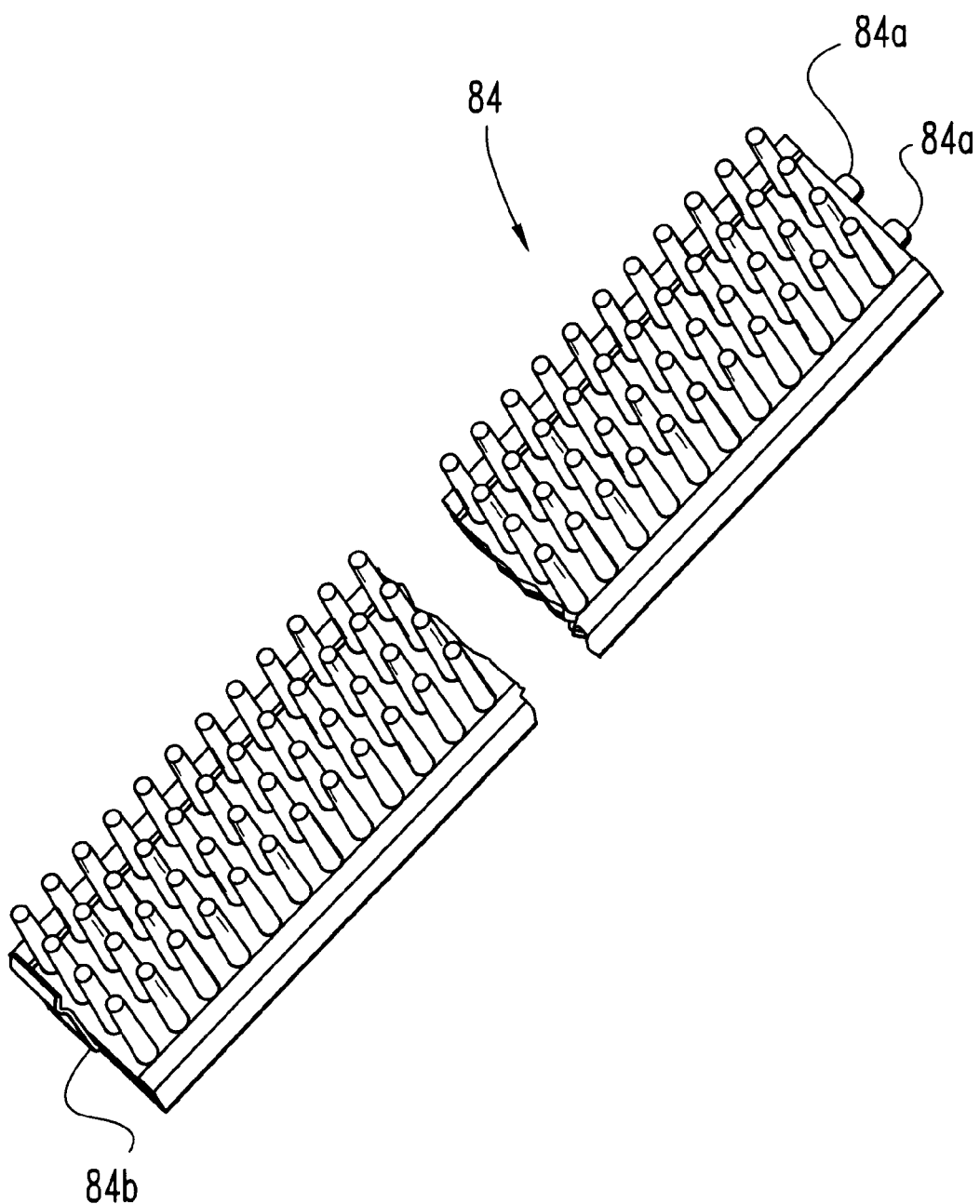
FIG. 20 is a perspective view of a finger mat which can be installed in the FIG. 1 instrument cassette.

Lower edge slots 75a and 75b in front sidewall 37 are cooperatively arranged with the button-hole apertures 76a and 76b in rear sidewall 38. As would be understood, slot 75a and aperture 76a are in straight line alignment as are slot 75b and aperture 76b. Each combination is constructed and arranged to receive a suitably-sized finger mat 84 (see FIG. 20). Finger mat 84 is constructed similar to the snap-in finger mat 46 disclosed in U.S. Pat. No. 5,279,800 which patent issued on Jan. 18, 1994 to Bernie B. Berry, Jr., and which patent is hereby expressly incorporated herein by reference. One end of the finger mat 84 includes two tabs 84a which fit into one of the two slots 75a or 75b. The opposite end includes a spring clip 84b which snap-fits into the aligned one of the two apertures, either 76a or 76b. This snap-fit assembly anchors the finger mat into the tray 21 and either one or two finger mats may be installed.

Figure 7:
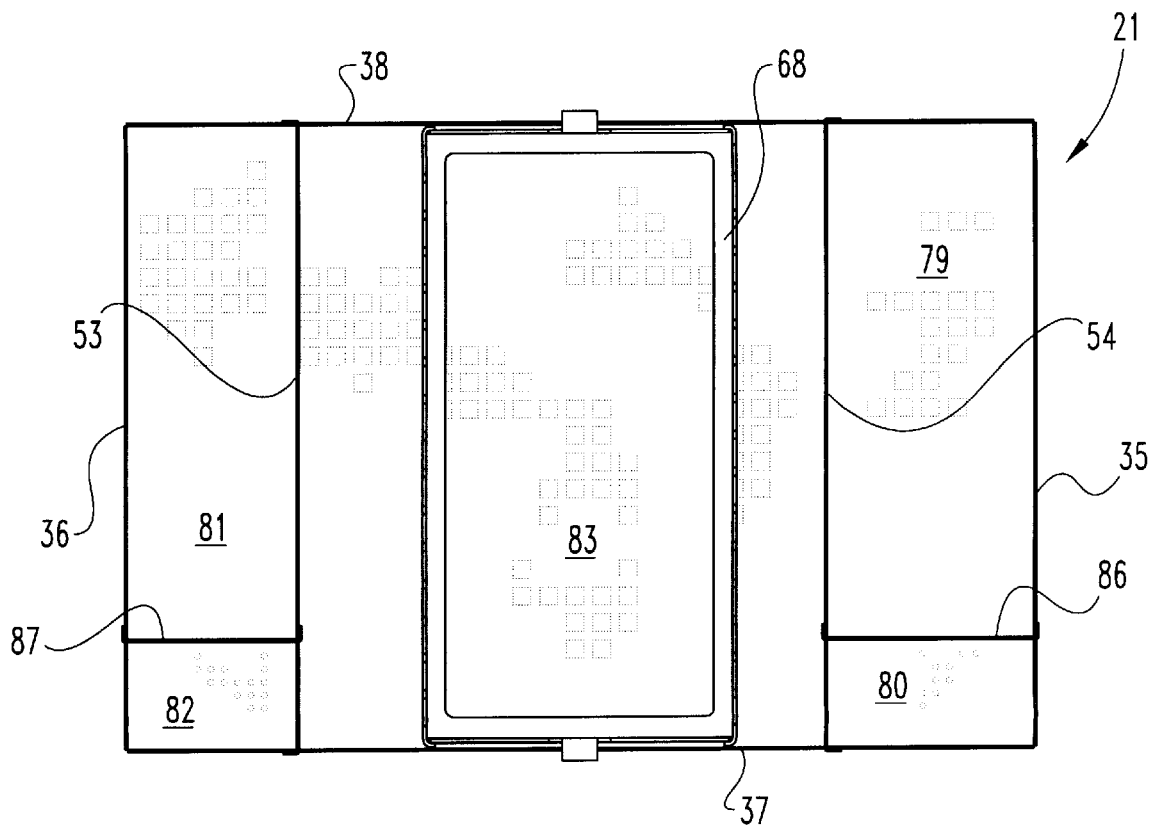
FIG. 7 is a top plan view of the tray portion of the FIG. 1 instrument cassette.

Referring to FIG. 7, the layout of interior space 40 is illustrated in greater detail. As illustrated, tray 21 is partitioned into various areas or compartments 79, 80, 81, 82, and 83. Tray 21 is substantially rectangular with sidewalls 35 and 36 being substantially parallel to each other and substantially perpendicular to sidewalls 37 and 38. In the preferred embodiment, tray 21 measures approximately 9 inches by 13 inches and is approximately 1.25 inches high (or deep) on each side. Divider 54 is positioned substantially parallel to sidewall 35 and shorter divider 86 (see FIGS. 13–15) extends between divider 54 and sidewall 35 and is substantially parallel to sidewall 37. This arrangement of dividers creates compartments 79 and 80. Compartment 79 measures approximately 3 inches by 7½ inches and compartment 80 measures approximately 3 inches by 1½ inches. Dividers 53 and 87 are arranged in a similar manner so as to define compartments 81 and 82. The only difference between the two sets of compartments is that compartments 81 and 82 are approximately ½ inch more narrow than compartments 79 and 80. Accordingly, compartment 81 measures approximately 2½ inches by 7½ inches and compartment 82 measures approximately 2½ inches by 1½ inches. The center compartment 83 measures approximately 7½ inches by 9 inches. The shorter dividers 86 and 87 are virtually identical with the exception of their length. There is an approximate ½ inch difference in the overall length between the two dividers as would be understood from the foregoing description regarding compartments 80 and 82. The longer dividers 53 and 54 include side edge tabs which are used to fit down into slots in sidewalls 37 and 38. Divider 54 fits into slots 52 and 63 while divider 53 fits into slots 51 and 62. The shorter dividers 86 and 87 also include a pair of oppositely-disposed tabs which fit into cooperating slots so as to secure the dividers in position. Divider 86 assembles into slots 55 and 88 while divider 87 assembles into slots 56 and 89. Additionally, each longer divider 53 and 54 includes a pair of base mounting tabs 90 and 91 (see FIG. 11) and each shorter divider 86 and 87 includes one base mounting tab 92 (see FIG. 14).

Figure 8:
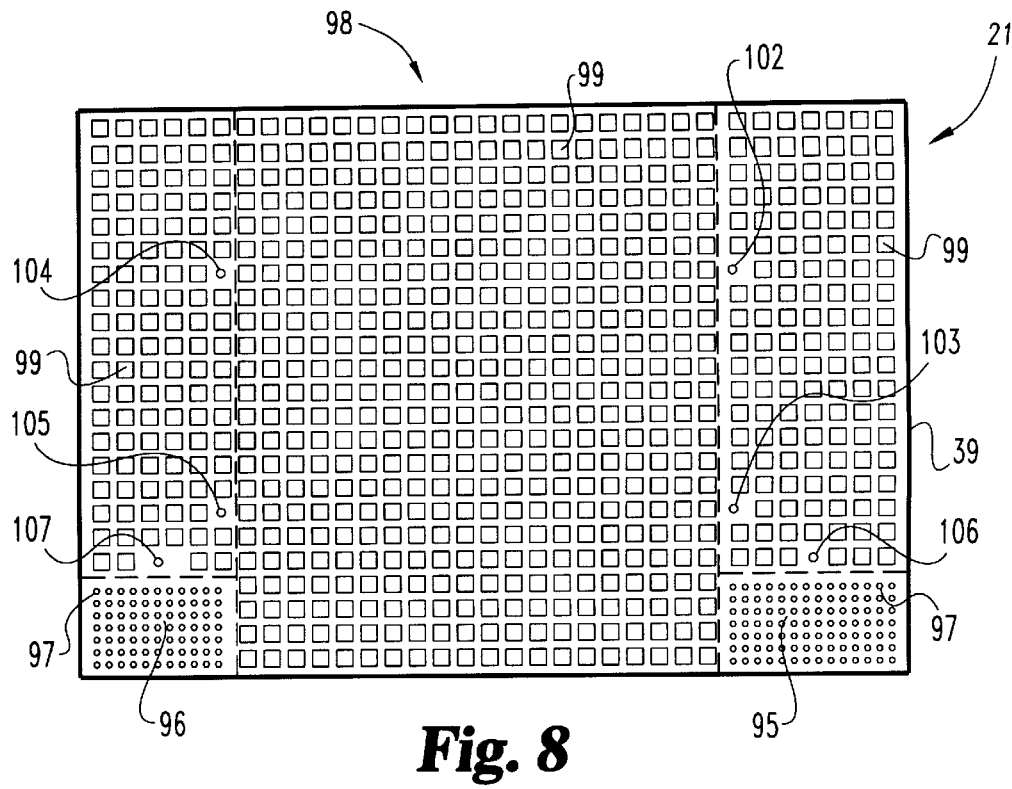
FIG. 8 is a top plan view of the FIG. 7 tray portion with the various dividers and instrument frame removed.

Referring to FIG. 8, the base panel 39 of tray 21 is illustrated in greater detail without the four dividers 53, 54, 86, and 87 installed and without the instrument frame 68 installed. Base panel 39 includes two generally rectangular areas 95 and 96 which have a uniform (i.e., equally-spaced rows and columns) pattern of small round holes 97. The two areas 95 and 96 have a size and shape which corresponds to compartments 80 and 82, respectively. The remainder, defined as area 98, includes a uniform pattern of substantially square apertures 99 which are each larger in area than are the small round holes 97. The grid which defines the pattern of square apertures includes a one-eighth wide web surrounding each aperture 99. While apertures 99 and holes 97 are each intended to permit the free passage of steam and/or sterilant into and out of instrument cassette 20, the smaller holes and areas 95 and 96 are suitable for retaining small parts and components which might otherwise pass through the larger square apertures 99.

In the general vicinity of divider 54 and on a line parallel to divider 54 there are two mounting holes 102 and 103. These two holes are used for the attachment of tabs 90 and 91 of divider 54. A similar pair of holes 104 and 105 are used for the mounting tabs of divider 53. Conventional threaded hardware is used and the screw heads on the exterior of base panel 39 provide feet for the cassette, thereby creating a slight ground clearance for improved drainage. Holes 106 and 107 are used for the base mounting tabs 92 of shorter dividers 86 and 87, respectively.

Figure 9:
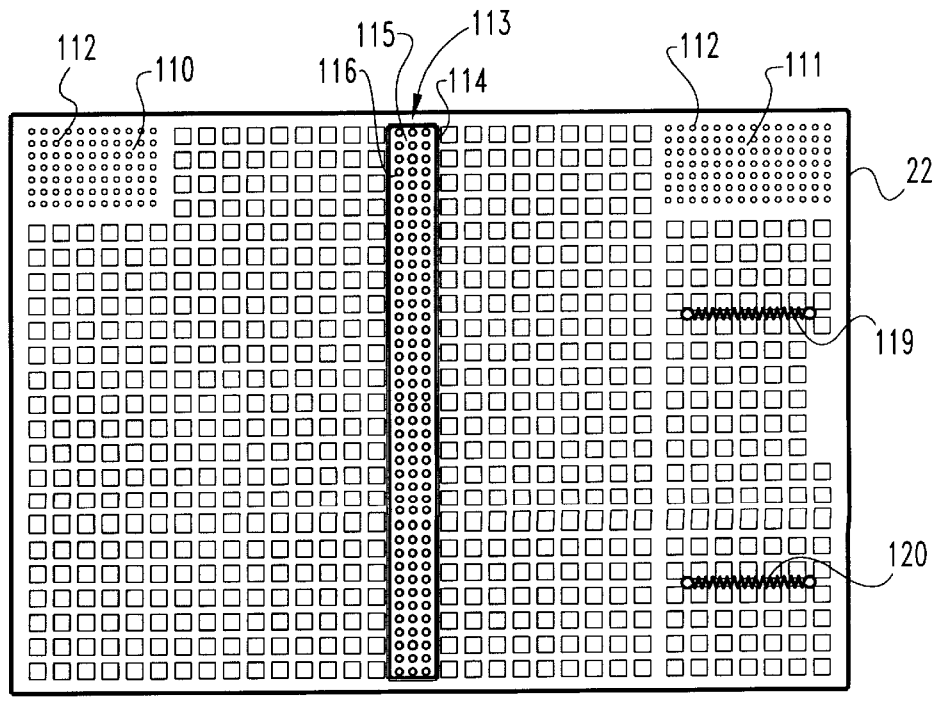
FIG. 9 is a bottom plan view of the lid portion of the FIG. 1 instrument cassette.

Referring to FIG. 9, the inside surface of lid 22 is illustrated in greater detail. Lid 22 includes two rectangular areas 110 and 111 which are arranged with a uniform pattern of small round holes 112. Area 110 corresponds in size, shape, and location to area 96 and area 111 corresponds in size, shape, and location to area 95. Finger mat 113 includes a metal frame 114 which snaps into position in lid 22 and a synthetic mat 115 with flexible fingers 116. The finger mat is sized and located so as to extend lengthwise across the center of lift-out frame 68. The location and length of fingers 116 are such that the fingers exert a moderate clamping pressure on whatever components or instruments might be retained in the sixteen instrument-receiving channels of lift-out frame 68.

Located above compartment 79 in lid 22 are two instrument-retaining springs 119 and 120. Each spring is an extension spring having a free length of approximately 1.75 inches. When extended to approximately 2.25 inches, there will be a slight clearance created between each pair of adjacent spring coils. The two springs, either individually or in combination, are constructed and arranged to receive instruments by simply lifting up on the spring and sliding an instrument underneath the spring. One spring is sufficient for smaller or shorter instruments. For larger of longer instrument, one portion of the instrument goes under spring 119 and a spaced-apart portion of the instrument goes under spring 120.

While the two springs 119 and 120 are able to be secured to the lid in a variety of ways, the preferred method is to hook each of the coiled ends around a selected one of the one-eighth wide webs which define each of the square apertures 99. It is intended for the mounting method to be easily removable and thereby changeable so that the location and spacing of the two springs can be changed. In fact, the number of springs can be increased as well as the length of the springs. It is therefore possible to customize lid 22 for whatever instruments, devices, or components are desired to be retained in the lid. The springs hold the item securely so that the lift can be removed and inverted without a concern that the items which are secured in the springs will fall out or otherwise come loose.

Referring to FIGS. 10–12, longer dividers 53 and 54 are illustrated. Divider 54 includes those features which have previously been described, including the mounting tabs 90 and 91, slot 55, and relief areas 57 and 58. Side tabs 121 and 122 provide the means of interfit for divider 54 into sidewalls 37 and 38. Divider 53 is virtually identical to divider 54 except for the location of slot 56 and the absence of the two relief areas. The mounting tabs extend into the interior of compartments 79 and 81 and the side tabs 121 and 122 extend in the same direction as the mounting tabs.

Figure 15:
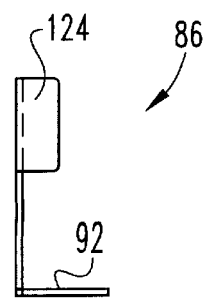
FIG. 15 is a side elevational view of the FIG. 13 divider.
Figure 13:
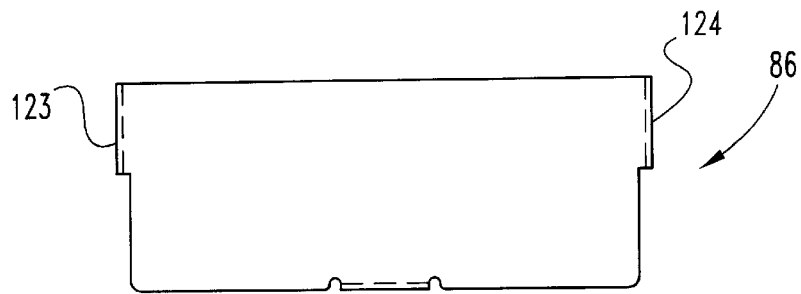
FIG. 13 is a front elevational view of a shorter divider comprising a portion of the FIG. 1 instrument cassette.
Figure 14:
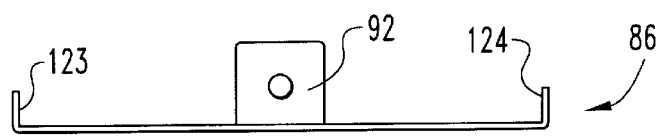
FIG. 14 is a top plan view of the FIG. 13 divider.

Referring to FIGS. 13–15, shorter divider 86 is illustrated in greater detail, including the oppositely-disposed tabs 123 and 124 which fit into slots 55 and 88, respectively. Divider 87 is virtually the same as divider 86, only shorter which corresponds with the more narrow width of compartments 81 and 82 as compared to the wider dimension of compartments 79 and 80.

Figure 16:
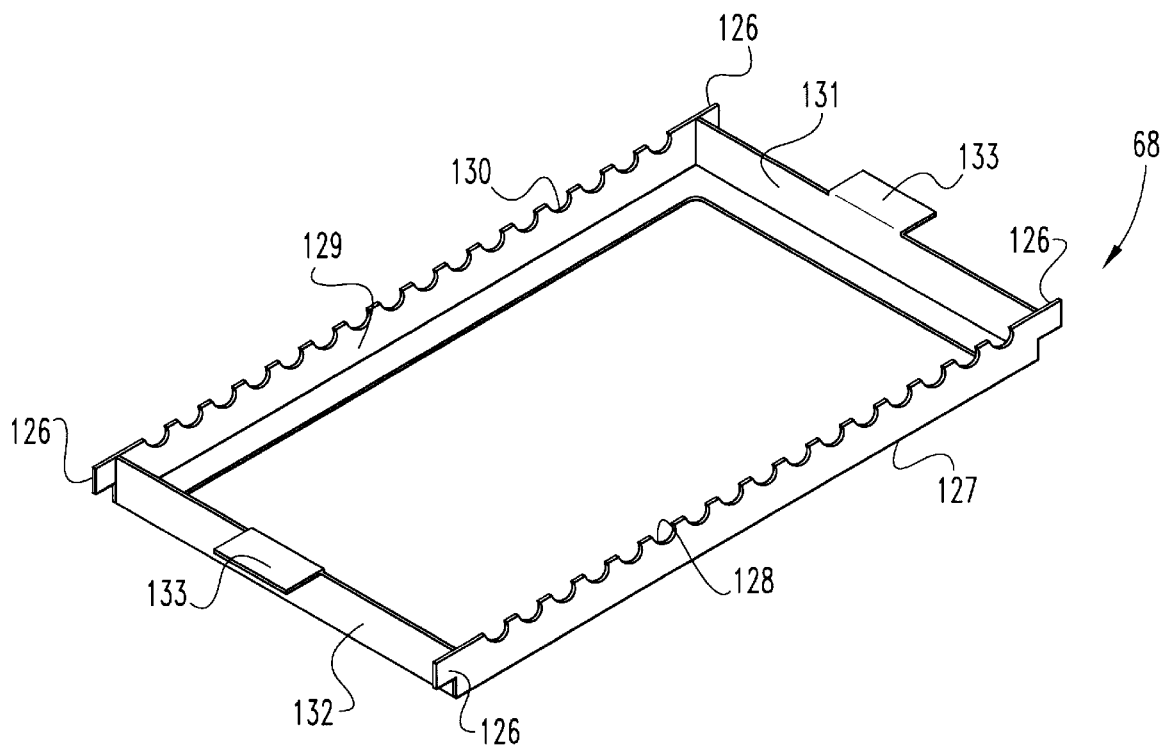
FIG. 16 is a perspective view of a lift-out instrument-retaining frame which comprises a portion of the FIG. 1 instrument cassette.

Referring to FIG. 16, lift-out rack or frame 68 is illustrated in greater detail. This unitary metal frame includes four corner tabs 126 which extend outwardly for receipt by one of the two four-slot arrangements in sidewalls 37 and 38. Side rail 127 is configured with sixteen instrument-receiving channels 128 and side rail 129 includes sixteen instrument-receiving channels 130. Channels 128 and channels 130 are aligned with each other for the receipt of the various instruments. The alignment of the receiving channels enables the instruments retained therein to assume an alignment or orientation whereby the longitudinal axis of each instrument is substantially parallel to ends 131 and 132. Each end includes a centrally-located lift tab 133 which provides a means of withdrawing the frame 68 from tray 21. The locations of the two lift tabs 133 coincide with the locations of relief areas 77 and 78.

Figure 17:
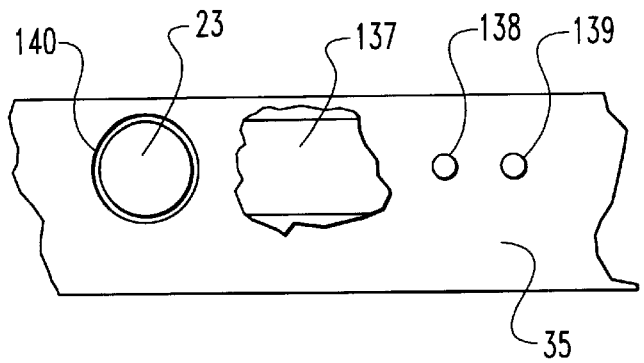
FIG. 17 is a partial, fragmentary, front elevational view of the right side of the FIG. 1 instrument cassette showing the spring-biased latch.

Referring to FIG. 17, the latch design for cassette 20 is illustrated in greater detail. Riveted to the inside surface of sidewall 35 is a latch bar 137 which extends from the two rivet locations 138 and 139 in the direction of compartment 80. A latch pin 23 is securely attached to the opposite end of latch bar 137. As should be understood, when the latch pin 23 is pushed inwardly in the direction of opening 140, the free end 141 of the latch bar flexes inwardly.

Figure 18:
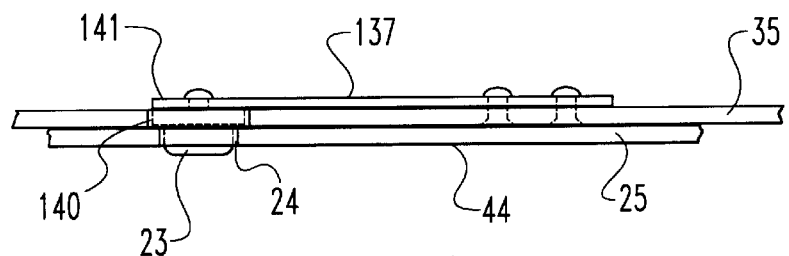
FIG. 18 is a diagrammatic top plan view in full section illustrating the FIG. 17 latch arrangement in cooperation with both the tray portion and the lid portion.

In the FIG. 18 illustration, the sidewall 44, including lip 25 and opening 24, have been added. The length of pin 23 is sufficient to extend beyond the outer surface of lip 25. As a consequence, any attempt to separate lid 22 from the tray 21 is blocked by pin 23. However, if pin 23 is pushed in far enough to clear the back edge of lip 25, then the lid 22 can be lifted up away from the tray (see FIG. 6). By providing latch bar 137 with sufficient size and stiffness, there is no risk that normal handling or vibration, including autoclaving, can cause the lid to inadvertently disengage from the tray. The latch design is secure and positive acting while at the same time providing a break away design when the latch pin is released. Importantly, the smooth and rounded edges of the exposed end of pin 23 and the low profile of pin 23 means that there is little or no risk that the sterile wrapping which will be applied to the autoclaved cassette can be punctured or torn due to the latch. The outer end of pin 23 extends beyond the outer surface of lip 25 only a short distance such that while it secures the lid to the tray, it does not create a protruding portion which could puncture any sterile wrapping. The end of pin 23 is the only portion of the latch pin assembly which extends into the lid.

Figure 19:
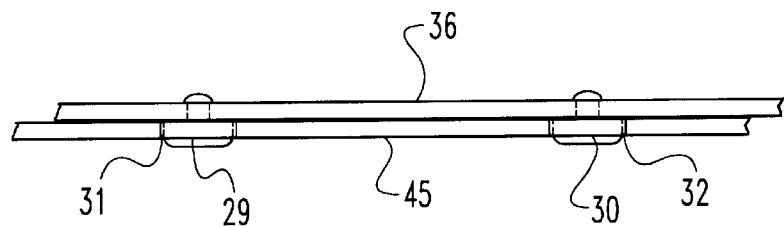
FIG. 19 is a diagrammatic top plan view of two retaining pins comprising a portion of the FIG. 1 instrument cassette.

Referring to FIG. 19, the relationship between pins 29 and 30 which are attached to sidewall 36 and their corresponding lid openings 31 and 23 is illustrated in greater detail. The heads of pins 29 and 30 extend minimally through openings 31 and 32 in the wall of lid 22. In this manner, the lid in this area cannot separate from the tray. With the lid securely anchored in position on the tray along sidewalls 35 and 36, there is no risk of separation. Like pin 23, the rounded design of pins 29 and 30 and their low profile (i.e., how far they extend out beyond the lid) means that there is no risk of puncture to the sterile wrapping.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An autoclavable instrument cassette for receiving and storing medical and dental instruments and equipment, said instrument cassette comprising:

a tray configured with a base and a plurality of side walls and including a plurality of separate compartments and a plurality of sterilant apertures;

a lid configured with a plurality of side walls and constructed and arranged to attach to said tray and to be separable from said tray, said lid including a plurality of sterilant apertures and a latch pin through opening defined by a first side wall which is one of said plurality of side walls of said lid;

a plurality of moveable instrument-retainer coil springs secured to said lid; and a latch pin assembly secured to a second side wall which is one of said plurality of side walls of said tray, said latch pin assembly including a latch pin which is constructed and arranged to extend through said second side wall into said latch pin through opening when said lid is closed onto said tray, said latch pin having a free end which is the only portion of said latch pin assembly extending through said first side wall.

2. The instrument cassette of claim 1 wherein said latch pin assembly includes a latch bar attached at a first end to said tray and attached at an opposite end to said latch pin.

3. The instrument cassette of claim 2 which further includes a retaining pin attached to said tray and a cooperating hinge pin opening defined by said lid.

4. The instrument cassette of claim 3 which further includes a plurality of dividers attached to the base of said tray, said plurality of dividers partitioning said tray into said plurality of separate compartments.

5. The instrument cassette of claim 4 which further includes a lift-out instrument rack which is constructed and arranged for holding a plurality of instruments.

6. The instrument cassette of claim 5 which further includes a snap-in finger mat secured in said lid and cooperatively arranged with said instrument rack to securely retain in position any instruments which are loaded into said instrument rack.

7. The instrument cassette of claim 1 which further includes a retaining pin attached to said tray and a cooperating retaining pin opening defined by said lid.

* * * * *